United States Patent [19]

Gardella, Jr. et al.

[11] Patent Number: 5,627,079
[45] Date of Patent: May 6, 1997

[54] REFUNCTIONALIZED OXYFLUORINATED SURFACES

[75] Inventors: Joseph A. Gardella, Jr., Buffalo, N.Y.; Terrence G. Vargo, Fairfax Station, Va.

[73] Assignee: The Research Foundation of State University of New York, Albany, N.Y.

[21] Appl. No.: 307,919

[22] Filed: Sep. 16, 1994

Related U.S. Application Data

[63] Continuation-in-part of Ser. No. 151,533, Nov. 12, 1993, abandoned, which is a continuation-in-part of Ser. No. 522,532, May 11, 1990, Pat. No. 5,266,309, which is a continuation-in-part of Ser. No. 328,852, Mar. 27, 1989, Pat. No. 4,946,903.

[51] Int. Cl.$^6$ ............................ G01N 33/543; H05H 1/00; B05D 5/00; B32B 27/00
[52] U.S. Cl. .................... 436/525; 436/518; 436/528; 436/531; 427/535; 427/569; 427/78; 427/96; 427/99; 427/255; 427/304; 428/615; 428/618; 428/620; 428/412; 428/421; 428/423.1; 428/424.6; 428/426; 428/429; 428/457; 428/480; 428/500; 428/523
[58] Field of Search ........................ 436/518, 524, 436/525, 527, 528, 531; 424/78.08, 78.09, 78.17; 427/77, 78, 96, 98, 99, 255, 299, 300, 301, 304, 305; 428/615, 618, 620, 621, 426, 421, 429, 448

[56] References Cited

U.S. PATENT DOCUMENTS

| | | | |
|---|---|---|---|
| 4,938,995 | 7/1990 | Giordano et al. | 427/41 |
| 4,946,903 | 8/1990 | Gardella et al. | 525/326.4 |
| 5,266,309 | 11/1993 | Gardella et al. | 424/78.09 |

OTHER PUBLICATIONS

D. T. Clark et al, J. Polymer Sci., Po. Chem. Ed., vol. 13, pp. 875–890, 1975.

Y. Haque et al, J. Appl. Polymer Sci., vol. 32, pp. 4369–4381, 1986.

F. V. Bright et al, Anal. Chim. Acta, vol. 262, pp. 323–330, 1992.

*Primary Examiner*—Ponnathapura Achutamurthy
*Attorney, Agent, or Firm*—Howard M. Ellis

[57] ABSTRACT

Permanently substituted oxyfluorinated surfaces can be formed on non-fluorinated substrates having a fluorinated surface or fluorocarbon coating applied by gas phase surface fluorination or plasma deposition. The oxyfluorinated surfaces can be refunctionalized by bonding organosilanes, isothiocyanate-containing fluorescent compounds and proteins, such as enzymes, antibodies and peptides directly to such surfaces. Surfaces refunctionalized with such protein based groups are useful in the fabrication of biological sensors, devices for separation of cell lines, filtration applications for selective binding of antigens. Masking techniques can be employed in forming a predetermined pattern of covered and exposed surfaces, for example, prior to oxyfluorination.

19 Claims, No Drawings

REFUNCTIONALIZED OXYFLUORINATED SURFACES

CROSS REFERENCE TO RELATED APPLICATION

This application is a continuation-in-part of application Ser. No. 08/151,533, filed November 12, 1993 now abandoned, which is a continuation-in-part of application Ser. No. 07/522,532, filed May 11, 1990, now U.S. Pat. No. 5,266,309, which is a continuation-in-part of application Ser. No. 07/328,852, filed Mar. 27, 1989, now U.S. Pat. No. 4,946,903.

BACKGROUND OF THE INVENTION

The present invention relates generally to fluorinated and non-fluorinated base materials or substrates having oxyfluorinated surfaces which can be reacted with other functionalities, such as organosilanes.

Fluorinated polymers, such as fluorohydrocarbon polymers, e.g. polyvinylidene fluoride, polyvinyl fluoride (PVF), including the well known fluorocarbon polymers, e.g., perfluorinated materials, such as PTFE, are characterized by extreme inertness, high thermal stability, hydrophobicity, and a low coefficient of friction as to resist adhesion to almost any material. While these properties are highly desirable, it would also be advantageous to modify some of the polymers' characteristics in order to expand the scope of their useful applications. For instance, in the field of biocompatible materials fluorocarbon polymers in various forms have been developed. But, because of their chemical inertness and extremely low reactivity the scope of improved devices, such as implantable prosthetic devices and probes has been limited. In the field of membranes and filters, fluoropolymers have also had limited applications due to low surface energy problems associated with these materials. Membranes and filters fabricated from PTFE, for example, are unable to selectively inhibit permeation of liquids with high surface tensions (>50 dynes/cm) while allowing liquids having lower surface tensions to pass through. PTFE has also been under intense study for applications in cell culture growth membranes, but a principal shortcoming has been the inability of cells to adhere to this low energy material.

Efforts of others to modify the properties of fluoropolymers have not been totally satisfactory. U.S. Pat. 4,548,867 (Ueno et al), for example, discloses a fluorine-containing synthetic resin having improved surface properties as evidenced by increased wettability with water, printability and susceptibility to adhesive bonding. The fluoropolymer is exposed to a low temperature plasma comprising an organic nitrogen-containing gas. Instead of modifying the atomic composition of the fluoropolymer starting material, Ueno et al form a thin "layer" of a nitrogen-containing wettable material thereto. Consequently, the adherence of such an overcoating tends to alter the microstructural morphology of the original polymer, especially with respect to pore size. This coating also alters desirable surface properties exhibited by the original fluorinated material.

Others have attempted the use of glow discharge and corona treatments to produce surface modifications. In some early work, Schonhorn and Hansen found that exposure of polyolefins and perfluorinated polymers to low power radio frequency electroless discharges in inert gas atmospheres produced favorable results over wet chemical methods. Their improvement in the bondability of surfaces was limited and attributed to the formation of a highly cross-linked surface layer. Studies of Hollahan et al, *J. Polym. Sci.*, 13, 807 (1969) aimed at rendering polymer surfaces biocompatible included the interaction of PTFE with plasmas excited in ammonia and nitrogen/hydrogen mixtures, the goal being the introduction of amino groups into the polymer surface. However, the long exposure times and high powers employed provided only limited results, and further, are taught to have produced significant changes not only in the surface chemistry, but also in the native bulk properties. Morphology of the surface was also severely effected.

In another ESCA study entitled "ESCA Study of Polymer Surfaces Treated by Plasma" Yasuda et al, *J. Polym. Sci., Polym Chem. Ed.*, 15, 991 (1977) the effects of discharges in argon and nitrogen on surface chemistry were considered on a range of polymers. PTFE was found to be particularly susceptible to defluorination and the introduction of oxygen and nitrogen moieties into the surface. Accordingly, there is a need for permanently modified homogeneous fluorinated polymers in which some of the original fluorine functionality is eliminated and replaced with oxygen functionality and hydrogen bonded to the carbon polymer backbone while substantially preserving the original surface morphology and bulk characteristics of the unmodified material on a molecular scale.

A further manifestation of the inert characteristics of highly fluorinated polymers has been their resistance to enter directly into reactions with other substances for purposes of introducing other functionalities and developing new properties not normally found in fluoropolymers. It has also been discovered that when fluoropolymers are exposed to radio frequency glow discharge (RFGD) in the presence of hydrogen gas-vapor (water, methanol or formaldehyde) mixture, a modified surface forms comprised of a controllably reduced amount of original fluorine with controlled amounts of hydrogen and oxygen or oxygen-containing groups covalently bonded to the carbon backbone of the polymer. The modified oxyfluoropolymers retain the unique properties of highly fluorinated polymers, such as PTFE, with the tendency to repel water and other polar solvents, high thermal stability, low adhesion and friction coefficients. However, unlike the modifications observed by Andrade et al (U.S. Pat. 4,508,606) and Ueno et al (U.S. Pat. 4,548,867) it has been found that the oxyfluoropolymers have reactive chemical sites which permit bonding with other chemical functionalities, such as organosilanes to form a class of novel and useful refunctionalized fluoropolymers. Accordingly, there is need for a series of novel and useful fluoropolymers having their surfaces oxyfluorinated and refunctionalized.

The foregoing oxyfluoropolymers impart a wide range of different and useful surface chemistries to the base fluoropolymer by enabling one to incorporate and/or fabricate sensor devices such that the non-stick, low energy properties of the base fluoropolymer substrate are preserved. The processes utilized for their manufacture have proven to be technologically simple to facilitate while enabling fabrication of devices which, for instance, are non-fouling and resistive to corrosion and/or weathering while simultaneously providing sensitivity to specific and selective molecules, biology or chemistry in a given environment. Representative examples include antibody based fiber optic devices for determining specific antigen concentrations in biologically diverse media, as well as protein and cell culture templates for adhesion and proliferation studies.

Ideally, it would be desirable to expand these capabilities to a broader range of materials which might already be in use in various technological areas, but are non-fluorinated. The problem, however, with refunctionalizing non-fluorinated materials is that often there is no simple, low cost direct route for producing a well defined and controlled interfacial modification equivalent to that produced with fluoropolymers. Such being the case, there is a need for non-fluorinated substrates and methods of manufacture which would include treatment for the addition of fluorine or fluorocarbon coatings thereto which are suitable for the addition of hydroxyl functionality, and which may also be refunctionalized.

In some instances, it may also be desirable to preserve the surface characteristics of the non-fluorinated substrates, for example, in conjunction with well defined boundaries or regions, e.g., stripes or patterns, while applying specific functional chemistries. Thus, the present invention also contemplates utilizing known masking techniques whereby fluorocarbon coatings are applied only to desired regions of the substrate with preferred dimensions ranging from 0.5μ or greater. Through known masking techniques regions of the substrate can be selectively defluorinated and refunctionalized according to methods previously disclosed without inducing changes throughout the entire substrate bordering these refunctionalized areas.

As a further extension of masking technology, in the field of electronics the ability to pattern electrical conduits and circuitry at the submicron level has become a major industry. This has been demonstrated almost exclusively, however, on ceramic and metallic materials which due to high dielectric constants and high surface energies are complicated with static charge build-ups resulting in current cross-talk and surface corrosion. The ability to utilize, for example, low dielectric materials, such as PTFE and FEP would advantageously reduce these problems and provide a significant technological advance in the field of high frequency, microwave microelectronics. But, due to economics and technical difficulties in processing fluoropolymers, such applications are likely to be restricted to highly specialized uses.

Both the economic and technical problems in this field of electronics can be bridged via the methods disclosed herein. That is, by modifying the fluorocarbon coatings applied to substrates by oxyfluorination and refunctionalization substrates can be formed for which processing and utilization are common in the electronics industry, but with the added benefit of a fluorocarbon based film with desirable dielectric and corrosion resistant properties.

SUMMARY OF THE INVENTION

It is one object of the invention to provide for novel oxyfluoropolymers in which the atomic structure of the native fluoropolymer material is permanently modified by the elimination of some of the original fluorine functionality and the introduction of both oxygen atoms or oxygen-containing groups and hydrogen atoms covalently bonded to the original carbon polymer backbone. The morphological properties of the oxyfluoropolymers at a molecular level remain substantially unchanged from those of the starting fluoropolymer material while wettability with respect to low surface tension liquids and surface free energy ($\gamma_s$) as determined through critical surface tension ($\gamma_c$) are increased. The fluoropolymer starting material used in preparation of the oxyfluoropolymers is intended to include fluorocarbon type polymers and fluorohydrocarbon polymers.

More specifically, it is an object of the invention to provide for novel oxyfluoropolymers having increased surface energies in which a portion of the surface fluorine atoms to depths of about 10 to about 100 Å of a fluoropolymer starting material are permanently substituted with hydrogen atoms, and from about 5 to about 20% of the fluorine atoms are also substituted with oxygen functionality. In this embodiment, instead of introducing a modified polymer coating to the original material, the object is to provide for oxyfluoropolymers in which the original starting bulk fluoropolymer material is permanently modified at the molecular level by removal of some of the fluorine so the carbon backbone has fluorine, oxygen and hydrogen atoms covalently bonded thereto. In essence, the bulk fluoropolymer material has a sufficient number of fluorine atoms permanently substituted with both hydrogen atoms and oxygen functionality covalently bonded to the carbon backbone to a surface depth of about 10 to about 100 Å to increase the surface free energy ($\gamma_s$) as determined through critical surface tension ($\gamma_c$) while the hydrophobic, non-fouling properties are maintained.

It is a further object of the invention to provide for oxyfluoropolymers in which up to 98 percent, and more specifically, from about 20 to about 85 percent of the surface fluorine atoms to depths from 10 to about 100 Å are permanently substituted with hydrogen and oxygen and/or oxygen-containing groups of which from about 3 to about 30 percent of the substituted fluorine is replaced with oxygen or oxygen-containing groups and from about 70 to about 97 percent is substituted with hydrogen atoms. The morphological properties and bulk properties of the oxyfluorinated surface of the polymer remain substantially unchanged over the starting bulk fluoropolymer material.

The permanently modified fluoropolymers have increased wettability towards low surface tension liquids, as well as chemically reactive sites allowing for attachment of various chemical functionalities to these normally inert surfaces, and as such have properties which make them especially adaptable for membrane applications, e.g. filtration membranes or other surface mediated processes, e.g., adhesion prevention or promotion; devices such as bioprobes coated with oxyfluoropolymers making them biocompatible while allowing specific ion permeability; expanded PTFE (ePTFE) membranes especially in the field of cell culture growth membranes; and because of improved and controlled wettability properties (with respect to wanted biological processes) implantable prosthetic devices, such as bone replacements, heart valves, and the like. Further, due to the retention of the inert hydrophobic properties these materials can be used such that little or no adsorption or fouling occurs from unwanted biological species.

It is yet a further object of the invention to provide for methods of making permanently modified fluoropolymers having increased surface energy by the steps of:

a) providing a starting fluoropolymer material;

b) providing a gas/vapor plasma mixture comprising hydrogen and at least one member selected from the group consisting of water, methanol and formaldehyde; and c) contacting the fluoropolymer material with the plasma mixture while exposing the fluoropolymer to at least one radio frequency glow discharge for a sufficient period to increase the surface free energy ($\gamma_s$) by permanently substituting to a depth from about 10 to about 100 Å on the starting fluoropolymer, fluorine atoms and hydrogen atoms and from about 20% of said fluorine atoms with oxygen functionality.

The methods impart surface wettability properties as well as chemically reactive sites to the original fluoropolymer without materially effecting the materials original hydrophobic properties. Plasma gas/vapor mixture concentrations of hydrogen, water, methanol, and formaldehyde together with wattage or power of the glow discharge and pressure (vacuum) are variables which determine the depth of surface modifications, as well as the respective atomic concentrations of carbon, fluorine, hydrogen and oxygen making up the modified portion of the final polymer.

The invention also contemplates refunctionalized oxyfluoropolymers comprising a fluoropolymer in which up to 98 percent of the surface fluorine atoms to depths from about 10 to about 100 Å have been permanently substituted with hydrogen and oxygen or oxygen-containing groups of which from about 3 to about 30 percent of the substituted fluorine has been replaced with the oxygen or oxygen-containing groups and from about 70 to about 97 percent of the substituted fluorine has been replaced with hydrogen atoms, and from about 3 to about 100 percent of the oxygen or oxygen-containing groups have a covalently bonded member selected from the group consisting of an organosilane, alkali metal or isothiocyanate-containing fluorophores.

As a further principal embodiment the invention includes oxyfluorinated substrates prepared from non-fluorinated substrates, such as fibers, films and sheets, consisting of either polymeric (non-fluorinated), ceramic, or metallic materials. The surface of the non-fluorinated polymer is modified either by fluorination through bonding of fluorine atoms, or by coating a fluorocarbon film thereto. The other substrates, i.e. ceramic and metallic types, also have their surfaces modified through fluorocarbon films. The fluorinated and fluorocarbon coated surfaces of the non-fluorinated substrates are oxyfluorinated whereby up to 98 percent of the newly added fluorine atoms to depths from about 10 to about 100 Å are permanently substituted with hydrogen and oxygen or oxygen-containing groups. From about 3 to about 30 percent of the substituted fluorine is replaced with oxygen or oxygen-containing groups and from about 70 to about 97 percent of the fluorine is replaced with hydrogen atoms. The morphological and hydrophobic properties of the oxyfluorinated surfaces remain substantially unchanged from the fluorinated or fluorocarbon film surfaces, i.e. prior to oxyfluorination, while wettability with respect to low surface tension liquids and surface free energy ($\gamma_s$) as determined through critical surface tension ($\gamma_c$) are increased.

The oxyfluorinated surfaces of the non-fluorinated substrates can be refunctionalized where from about 3 to about 100 percent of the oxygen or oxygen-containing groups have covalently bonded either an organosilane, an isothiocyanate-containing fluorescent compound or a protein, such as an enzyme, antibody or peptide. In the case of substrates having oxyfluorinated surfaces refunctionalized with a protein the invention contemplates bonding proteins directly to the modified surface without requiring organosilane coupling agents according to the methods of Frank B. Bright et al, *Analytica Chimica Acta*, 262 (1992) 323–330.

Substrates having oxyfluorinated surfaces refunctionalized with proteins find applications as sensors. For example, immobilization of the hydrolase enzyme urease through bonding to an oxyfluoropolymer provides surfaces which are useful in selective biosensory recognition elements for the determination of urea. Such sensors have important applications in the diagnosis of renal disease and for control of artificial kidney dialysis.

Substrates of the invention refunctionalized with immobilized proteins also find applications as sensors which utilize an ion selective field effect transistor (ISFET) as the transducing element. In this application the ISFET is coated with an oxyfluoropolymer created on a plasma deposited fluoropolymeric thin film. Urease is then covalently bonded directly to the oxyfluorinated surface according to the refunctionalization methods described herein. Such articles are useful as recognition elements for detecting and quantifying urea. Immobilized proteins also find applications as sensors which utilize various metals and metal/ oxide enzyme electrodes, e.g. iridium, tungsten and antimony, as the transducing elements. Metal electrodes can be coated with an oxyfluoropolymers created on plasma deposited fluoropolymeric thin films. Urease is then covalently bonded directly to the oxyfluorinated surface as a recognition element for detecting and quantifying urea.

The protein refunctionalized oxyfluorinated surfaces also find applications in the filtration of toxins using oxyfluoropolymer membranes having immobilized enzymes or antibodies which selectively bind particulate antigens, i.e. toxins. They also have biomedical applications by covalent immobilization of minimal peptide sequences to oxyfluorinated surfaces; as immobilized peptide sequences for separation of cell lines, and as titanium hip and dental implants coated with plasma deposited fluoropolymer films, and so on.

As a further embodiment, the invention contemplates substrates having well defined boundaries or regions (e.g., stripes or patterns) in such instances where it is desirable to preserve surface characteristics of a polymeric, ceramic, or metallic surface. Using known masking techniques fluorocarbon films, for instance, can be initially applied to only the desired regions of a substrate. The coated regions are selectively defluorinated and oxygen functionality and hydrogen atoms bonded to the fluoropolymer backbone through the oxyfluorination methods described herein. Hydroxyl groups and other oxygen functionalities are then refunctionalized without inducing changes in the base materials' surfaces bordering the refunctionalized regions.

It is also an object of the invention to provide for products and processes of preparing substrates with homogeneous fluorocarbon coatings where, for example, it is desired to reduce surface energy, decrease dielectric properties of the surface, or enhance weatherability with the simultaneous addition of patterned regions of different chemistry. In such instances, masking can be applied after fluorination or application of a fluorocarbon coating to a substrate. The surface can be masked to the desired pattern, selectively defluorinated by oxyfluorination methods described herein and refunctionalized to introduce an organosilane, or other desired functionality to the exposed surface to produce regions bordering areas having low dielectric and corrosion resistant properties characteristic of the unmodified fluorocarbon surface.

It is still a further object to provide methods of making refunctionalized oxyfluorinated substrates by the steps of:

a) providing a non-fluorinated base material, either a polymeric, ceramic, or a metallic material, e.g., metal or metal alloy;

b) modifying the surface of:
   (i) the polymeric base material by fluorination or by coating with a fluorocarbon film;
   (ii) the ceramic and metallic substrates by coating with a fluorocarbon film;

c) oxyfluorinating the modified surface of (b) with a gas/vapor plasma mixture comprising hydrogen and at least one other member selected from either water, methanol and formaldehyde while exposing the substrate to at least one radio frequency glow discharge under vacuum for a sufficient period to substitute at least a portion of the fluorine atoms on the substrate to a depth from about 10 to 100 Å with covalently bonded hydrogen and oxygen atoms or oxygen-containing groups, and d) refunctionalizing the oxyfluorinated surface of (c) by reacting at least a portion of the oxygen atoms or oxygen-containing groups on the substrate with either an organosilane, an isothiocyanate-containing fluorescent compound or a protein.

The methods of the invention include the step of masking portions of the modified surface of step (b) to form a pattern of covered and exposed surfaces whereby the exposed surfaces are oxyfluorinated and refunctionalized according to steps c–d.

It is still a further object of the invention to provide a method of making a patterned refunctionalized oxyfluorinated substrate by the steps of:

a) providing a substrate comprising a fluorinated material;
b) masking portions of the substrate of step (a) to form a predetermined pattern of covered and exposed surfaces;
c) oxyfluorinating the masked surface of step (b) with a gas/vapor plasma mixture comprising hydrogen and at least one other member selected from the group consisting of water, methanol and formaldehyde while exposing the substrate to at least one radio frequency glow discharge under vacuum for a sufficient period to substitute at least a portion of the fluorine atoms on the exposed surface to a depth from about 10 to 100 Å with covalently bonded hydrogen and oxygen atoms or oxygen-containing groups;
d) refunctionalizing the substrate of step (c) by reacting at least a portion of the oxygen atoms or oxygen-containing groups on the exposed portions of the substrate with a member selected from the group consisting of an organosilane, an isothiocyanate-containing fluorescent compound and a protein.

DETAILED DESCRIPTION OF THE INVENTION

The invention pertains to surfaces or substrates, either that of bulk fluoropolymers or non-fluorinated materials, such as non-fluorinated polymeric materials, like thermosetting and thermoplastic resins and plastics in the form of fibers, films and sheets, for instance.

Useful fluoropolymer starting substrates include both fluorocarbon polymers and fluorohydrocarbon polymers. This would include fluoropolymers having a carbon backbone with atoms bonded thereto consisting of either fluorine or both fluorine and hydrogen provided that when hydrogen atoms are present fluorine shall also be present in a ratio of at least 1:3. Preferably, the fluoropolymers include materials having a critical surface tension ($\gamma_c$) ranging generally from about 15 to about 30 dynes/cm. Specific representative examples of useful low surface energy fluorocarbon polymers are the perfluorinated polymers, e.g., polytetrafluoroethylene (PTFE), polymers of hexafluoropropylene and tetrafluoroethylene like fluorinated ethylene-propylene (FEP) copolymers, etc. Suitable low surface area fluorohydrocarbon starting polymers include resins like polytrifluoroethylene, poly(vinylidene fluoride) (PVDF), poly(vinyl fluoride), poly(vinyl difluoride), including piezo and pyroelectric poled PVDF, and the like.

Representative non-fluorinated thermosetting materials include the phenolic, aminoplast and epoxy type resins, to name but a few. Thermoplastic materials include a broader range of resinous materials including, but not limited to the polyolefins, like polyethylene, polypropylene; acrylic resins which include esters of acrylic or methacrylic acids, sometimes modified with non-acrylic monomers, such as the ABS group. The acrylates typically include methyl, ethyl, butyl and 2-ethylhexyl esters. Representative methacrylates are the methyl, ethyl, butyl, lauryl and stearyl esters. Other useful non-fluorinated thermoplastic substrate base materials are the polycarbonate resins, polyurethanes, polyesters, polystyrene, PVCs, and so on.

Other useful non-fluorinated base materials or substrates include ceramic materials and metallic materials, such as gold, nickel, copper, aluminum, non-ferrous alloys and ferrous alloys, such as steel, i.e. low and high carbon steel alloys, stainless steels, like SS316L and SS304L. Representative non-ferrous alloys include the nickel based alloys available under well known trademarks Monel®, Hastelloy® and Inconel®.

Ceramic substrates may include classes of non-fluorinated materials such as alumina, corderite, fosterite, porcelain (zircon), steatite, titanates (Ba, Sr, Ca, Mg and Pb), titanium dioxide, vitreous silica, borosilicates, quartz, and zinc crown glasses, to name but a few. Included within the ceramic substrates are the conductive, semi-conductive and dielectric materials, which are materials based on either oxides, carbides, nitrides and borides. Representative examples of non-fluorinated ceramic conductive ceramics substrates contemplated are titanium nitride and titanium boride; semi-conductive ceramics include such representative examples as metal silicides like titanium silicide, tantalum silicide and tungsten silicide, and metal oxides like tin oxide, zinc oxide and copper oxide. Non-conductive ceramic materials include substrates containing glasses from the class of silicon oxides ($SiO_2$).

In order to refunctionalize, the above non-fluorinated substrates must first be treated by adding fluorine or fluorocarbon coatings in the form of films which are suitable for oxyfluorination and the addition of hydroxyl functionality. Non-fluorinated polymers, such as the polyolefins, for example, can have their surfaces fluorinated by either gas-phase surface fluorination processes or coated with a fluorocarbon based plasma film. Both processes are well known and documented in the prior art. Typically with gas phase fluorination polymers are exposed to a mixture of fluorine and nitrogen whereby fluorine atoms become bonded to the polymer surface at the molecular level. Lagow and Margrave, *Progr. Inorganic Chem.*, Ed. S. J. Lippard, 26 (1979) 161 disclose methods of gas phase surface fluorination for providing antireflective, low surface energy films to various commercially available base polymers, such as highly cross-linked polyethylene, polypropylene, poly (methyl methacrylate), polycarbonate, polyester, polystyrene and polymethylpentene. D. T. Clark et al, *Jour. Polym. Sci.*, Polymer Chem. Ed., Vol. 13, 857–890 (1975) also disclose the surface fluorination of high density polyethylene films. The contents of both publications are hereby incorporated-by-reference herein. Other representative enabling publications relating to gas phase fluorination methods include U.S. Pat. Nos. 3,988,491 and 4,020,223.

Methods for preparing fluorocarbon plasma deposited films are also well documented in the literature. For instance, Haque and Ratner, *Jour. App. Polym. Sci.*, Vol. 32, 4369–4381 (1986) disclose suitable methods for modification of polymer surfaces with plasma deposited thin films using a capacitatively coupled RF-discharge system. Representative useful fluorinated gaseous materials include hexafluoroethylene, perfluoropropane and hexafluoropropene. K. Nakajima et al, *Jour. App. Polym. Sci.*, Vol. 23, 2627–2637 (1979) disclose methods for applying plasma polymerized fluorocarbon coatings which can be utilized for generating surfaces having low dielectric and non-corrosive properties, etc. U.S. Pat. 4,718,907 to Karwoski et al disclose useful methods for introducing fluorinated coatings for vascular grafts and other biomedical technologies. The foregoing publications relating to methods for applying plasma deposited fluorocarbon coatings are incorporated-by-reference herein.

It is to be understood that all other non-fluorinated substrates, in addition to the non-fluorinated polymers, i.e., ceramic and metallic based substrates of the invention, can be coated with fluorocarbon based plasma films by the methods previously discussed.

Regardless whether the starting substrate is that of a bulk fluoropolymer or a non-fluorinated material which has been surface fluorinated or treated with a deposited fluoropolymeric film, it is necessary to permanently oxyfluorinate the material. This is accomplished through radio frequency glow discharge whereby the top 10 to about 100 Å of the fluorinated or fluorocarbon surface material is permanently modified by substitution of a portion of the surface fluorine functionality with oxygen or oxygen-containing groups and with hydrogen covalently bonded to the carbon polymer backbone. By regulating amounts and ratios of carbon, fluorine, oxygen and hydrogen in the treated surface, surface energy can be increased from that of the original material along with wettability towards non-polar aliphatic liquids without materially altering the corresponding hydrophobic properties of the fluorinated or fluorocarbon surface, or altering surface morphology and bulk characteristics.

The oxyfluorinated surface compositions are especially unique in that a controllable amount from about 1 to about 98% of the fluorine atoms of the fluorinated or fluorocarbon material's surface interface are permanently removed and replaced with hydrogen atoms and with oxygen atoms or low molecular weight oxygen-containing functionalities, so that all substituents are covalently bonded directly to the carbon backbone polymer chain to a depth of about 100 Å. Oxygen functionality may take the form of oxo, hydroxyl, alkoxy, like methoxy, ethoxy and propoxy or R'—CO— or combinations thereof where R' is hydrogen or alkyl, and particularly $C_1$–$C_5$ lower alkyl, including methyl, ethyl, propyl, isopropyl, and so on. Accordingly, unlike the nitrogen-containing monolayers/surface overcoatings of U.S. Pat. 4,548,867 the intrinsic atomic composition of the above substrates is permanently modified to regulated surface depths ranging from about 10 to about 100 Å, providing a novel combination of properties, i.e., chemically reactive sites, greater surface wettability and free energy enhancement of fluorinated polymers and nonfluorinated materials, including polymeric materials having fluorinated surfaces, as well as ceramic and metallic substrates with deposited thin films while still substantially preserving the hydrophobic properties and microstructural morphology, e.g. membranous structure, pore size, surface roughness on a molecular scale, etc., of the fluorocarbon surfaces prior to oxyfluorination.

The oxyfluorinated polymers and non-fluorinated substrates with oxyfluorinated polymer surfaces produce a wide variety of surface free energy increases over the starting fluorinated materials where, for example, a fluoropolymer like PTFE with a $\gamma_c$ of about 18 dynes/cm at 20° C. can be increased to about 40 dynes/cm to a depth of between 10 to 100 Å for increased wettability, and other surface properties relating to the surface free energy of a substrate. Even with such increases in surface free energy the hydrophobic properties of the substrate prior to oxyfluorination remain substantially intact. That is, the oxyfluorinated surfaces of the substrates having hydrogen, oxygen and fluorine functionalities are covalently bonded to the carbon backbone of the polymeric surface will still inhibit surface fouling, permeation and wetting by liquids with high surface tensions, i.e., >50 dynes/cm, like water and other similar polar solvents, but also being wettable by liquids having low surface tensions, i.e., <50 dynes/cm, such as blood plasma and other nonpolar organic solvents. This is quite unexpected because when the surface free energy of a polymer is increased one normally finds with the increase in wettability an equivalent decrease in the hydrophobic properties of the substrate occurs. However, quite surprisingly with the increased surface energy of the oxyfluorinated surface wettability is increased without the normally expected decrease in hydrophobicity from that of the original starting material.

The oxyfluorinated surfaces are prepared by a plasma treatment process in which the previously described surface fluorinated polymers and fluorocarbon coated non-fluorinated substrates are exposed to a single or a series of relatively low power radio frequency discharges (RFGD). The target substrates generally can be in the form of a sheet, premolded or coated article, such as membrane or filter, e.g. Goretex®, where, for example, increased permeability of ions would be desirable without altering pore characteristics of the native material; a bioprobe of conventional design coated with Teflon® or a molded, implantable prosthetic device where, for instance, it would be desirable to modify its adhesive and/or surface reactivity characteristics to blood platelet attachment.

Instead of a plasma treatment with purely a gas the radio frequency glow discharge is conducted in an atmosphere of a gas/vapor mixture at pressure vacuums of under 1,000 mTorr, and more preferably, from about 50 to 200 mTorr, and power loadings of less than or equal to 100 watts.

Although not wishing to be held to any precise mode of action, the primary mechanism of the plasma treatment process of the instant invention is believed to involve the transfer of energy to the gaseous ions directly to form charged ionized gas species. The radio frequency glow discharge plasma gas ions become excited through direct energy transfer by bombarding the gas ions with electrons. Thus, by exposing the fluoropolymer material, non-fluorinated substrates with fluorinated surfaces or fluorocarbon coatings to either a single or a series of radio frequency glow discharge gas/vapor plasmas consisting of admixtures of hydrogen gas ranging from 20% to 99% by volume, and 1 to about 80% by volume of a vapor from liquids, such as water, methanol, formaldehyde and mixtures thereof, 1 to about 98% of the surface fluorine atoms are permanently removed in a controlled/regulated manner and replaced with oxygen atoms or low molecular weight oxygen-containing functionality along with hydrogen atoms. Although hydrogen is required, in all instances, by itself it is insufficient to introduce both hydrogen and oxygen moieties to the carbon polymer backbone. A non-polymerizable vapor/$H_2$ mixture is necessary to introduce the required hydrogen and oxygen or functionalized oxygen moieties onto the fluorinated surface without disrupting surface morphology. Further, uses of pure gas mixtures, specifically $H_2/O_2$ show only limited results. Representative radio frequency glow discharge plasmas and operating conditions are provided in Table I below:

TABLE I

| Starting Material | RFGD Mix Composition | Pressure (mTorr) | Time (Min.) | Depth (Å) | C/O | C/F | F/O | Stoichiometry |
|---|---|---|---|---|---|---|---|---|
| Unmodified PTFE* | — | — | — | — | — | 0.45 | — | $C_2F_{2.3}$ |
| Unmodified PVDF | — | — | — | — | — | 1.0 | — | $C_1F_1$ |
| Modified PTFE | 2% (vol) $H_2O$/98% $H_2$ | 150 | 20 | 100 | 7.5 | 1.5 | 5.0 | $C_{15}F_{10}H_{18}O_2$ |
| Modified PTFE | 2% (vol) $H_2O$/98% $H_2$ | 200 | 10 | 100 | 8.6 | 0.91 | 9.7 | $C_{17}F_{19}H_{13}O_2$ |
| Modified PTFE | 20% (vol) Methanol vapor/80% $H_2$ | 150 | 30 | 100 | 3.0 | 1.5 | 2.0 | $C_6F_4H_6O_2$ |
| Modified PTFE | 20% (vol) Methanol vapor/80% $H_2$ | 200 | 5 | 100 | 9.3 | 2.0 | 4.7 | $C_{28}F_{14}H_{39}O_3$ |
| Modified PVDF | 2% (vol) $H_2O$/98% $H_2$ | 200 | 10 | 100 | 8.0 | 16.0 | 0.48 | $C_{16}F_1H_{29}O_2$ |

*Porous Goretex membrane

Through specific and controlled addition of oxygen functionality via radio frequency glow discharge the oxyfluorinated surfaces disclosed herein are resistant to fouling and adsorption of substances, a property which is consistent with the unmodified bulk fluoropolymers, surface fluorinated polymeric substrates or non-fluorinated substrates with deposited fluorocarbon films.

However, unlike unmodified fluorinated surfaces it was found that the oxyfluorinated surfaces have the unique ability to react cleanly and rapidly with various atoms, molecules or macromolecules through the oxygen-containing groups on the surfaces, i.e. hydroxyl, carboxylic acid, ester or aldehyde to form refunctionalized oxyfluorinated surfaces on the fluoropolymer and non-fluorinated substrates.

This is especially advantageous because generally fluorinated materials are inert to wet and physical-chemical processes, at least to those which do not also induce substantial surface morphological damage. In addition, due to the relative inertness of oxyfluorinated surfaces the ability to incorporate reactive functionality onto their surfaces creates a material which is specifically and controllably reactive while also being inert to other chemical and environmental concerns, i.e. adsorption of surface contaminants. In addition to the useful applications discussed above, the refunctionalized bulk fluoropolymers, refunctionalized surface fluorinated polymeric substrates and refunctionalized non-fluorinated substrates with deposited fluorocarbon films are useful as coatings and films, and in fiber optics, optoelectronic and biomedical devices, such as biosensors and antibody sensors. They also have uses in general applications as non-fouling substrates which can have optically, electrically, electrochemically active sensor molecules attached. The refunctionalized oxyfluoropolymers are also useful as separators and membranes in various electrochemical devices, such as batteries.

The types of functionalities which can be utilized with the oxyfluorinated surfaces include all those which can be reacted with hydroxyl, carboxylic acid, ester and aldehyde groups bonded through the fluoropolymer backbone by means of reactions generally familiar among those skilled in the art. The reactivity of the oxyfluorinated surface is determined by the particular type of oxygen functionality. For instance, silanes of the silicon-containing organic, i.e. organosilanes or ligand bearing organosilane coupling agents or inorganic classes react vigorously with hydroxyl groups forming a silanol linkage or coupled bond. However, the rate of reaction is enhanced even further due to the close proximity of the reactive oxygen functionality to the electronegative fluorine atom(s). Apparently, this provides for extremely rapid reaction rates through stabilization of the oxygen anion. The preferred refunctionalized oxyfluorinated surfaces may be prepared with a wide range of ligand bearing organosilane coupling agents, i.e., organosilanes of the general formula:

$$Y(CH_2-)_n-Si-(X)_3 \quad (I)$$

in which Y is a member selected from the group consisting of allyl, alkyl, haloalkyl, amino, mercapto, epoxy, glycidoxy, methacrylate, cyano and $—CH_2CO_2$ alkyl, and n is from 0 to about 17 and X is independently selected from hydrogen, halogen, alkyl, haloalkyl, alkylamino, alkoxy and trialkylsiloxy. The silane coupling agents are known materials which are commercially available through ordinary channels of commerce, such as Petrarch Systems, Bristol, PA.

The process of preparing organosilicon substituted oxyfluorinated surfaces can be illustrated by the following reaction:

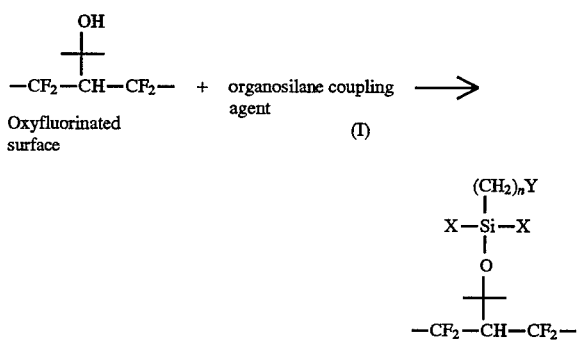

wherein the values for X, Y and n are the same as formula (I).

In addition to the ligand bearing organosilane coupling agents (I), the refunctionalized oxyfluorinated surfaces are preferably formed from organosilane coupling agents in which Y is alkylamino, dialkylamino, mercapto or glycidoxy and in which X is chlorine, bromine, fluorine, alkyl having from 1 to 4 carbon atoms, chloromethyl, monoethylamino, dimethylamino, methoxy, ethoxy, propoxy, butoxy or trimethylsiloxy. Specific representative ligand bearing organosilanes are 3-aminopropyltriethoxysilane, 3-mercaptopropyltrimethoxysilane and 3-glycidoxypropyltrimethoxysilane, to name but a few.

There are several classes of substances whose molecules, under appropriate conditions, self-assemble to form thin films which act as spacers on the oxyfluorinated surfaces. In general, these self-assembling molecules characteristically include a polar end group, a non-polar group on the opposite end with a reactive moiety at or near the terminus, and an intermediate region typically composed of saturated or unsaturated hydrocarbon chains. The class of polar end groups which interact with the oxyfluorinated surfaces include silanes of the $R_nSiX_m$ type wherein where R is an organic functional group; n is a number between 1, 2 or 3; m=4−n; and X is halogen, alkoxy or amines. The class of polar end groups further includes carboxylic acids, acid chlorides, anhydrides, sulfonyl groups, phosphoryl groups, hydroxyl and amino groups. The class of non-polar end groups includes olefins, acetylenes, diacetylenes, acrylates, aromatic hydrocarbons, methacrylates, methyl, perfluorinated hydrocarbons, primary amines, long chain hydrocarbons and esters.

It will be understood any of the base substrates discussed herein including non-fluorinated substrates surface fluorinated or those having plasma deposited fluorocarbon coatings can be patterned by first applying RFGD treatment using hydrogen/water or hydrogen/methanol plasmas. The first step includes placing the fluorinated substrate in an RFGD reactor with a metallic grid, e.g. nickel, to oxyfluorinate only those regions exposed or not covered by the metallic grid. This method enables spatially limited patterned regions having spatial resolutions on the order of 1 to 5 μm. Once completed, silanization will occur only on those areas which were initially exposed to the RFGD plasma.

Other particularly useful functionalities which may be covalently bonded with the oxyfluorinated surfaces through their reactive oxygen-containing sites are the fluorophores which refers to a group of organic compounds that may fluoresce. The preferred fluorophores are the isothiocyanate substituted types, such as fluorescein isothiocyanate (FITC), malachite green isothiocyanate, rhodamines like tetramethylrhodamine isothiocyanate (TRITC), and the like, which are described in the publication by Molecular Probes, Inc., entitled *Handbook of Fluorescent Probes and Research Chemicals* by Richard P. Haughland, 1989, which publication is incorporated-by-reference herein. The isothiocyanate modified fluorescent compounds are also available from Molecular Probes, Inc. The oxyfluorinated substituted isothiocyanate fluorescent materials are especially useful in a wide variety of probes and sensors, such as for nucleic acids.

In addition to the organosilicon and fluorophore substituted fluorinated surfaces, other representative examples include alkali metal derivatives of oxyfluorination:

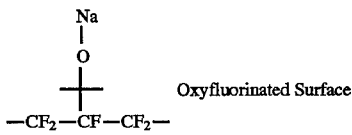

In addition to sodium oxyfluorinated surfaces, solutions of potassium and lithium hydroxide may be reacted with the oxygen-containing groups of the oxyfluorinated surfaces for purposes of preparing useful alkali metal oxyfluorinated surfaces which can then be used in electrochemical cells, including energy producing cells, like batteries and as cell separators.

The oxyfluorinated surfaces are also unique in view of their ability to react with proteinaceous materials, and particularly enzymes, antibodies and peptides. One advantage lies in the discovery that such biological materials can be bonded directly to substrates without organosilane coupling agents, like APTES or GOPS. This should increase stability and regenerability in that the low surface energy of the oxyfluorinated surface is better preserved in the case where no intermediate silane coupling agent is used to facilitate immobilization. Further, molecules possessing selective binding sites can be better oriented with respect to having their receptor site exposed away from the oxyfluorinated surface than when the molecules are reacted to non-ordered silane coupling films as in the work of Bright et al supra.

Clearly, this ability to directly immobilize sensor molecules to oxyfluorinated surfaces has a direct and novel impact on sensor technology, but it can also be applied to chromatographic separation technology which is based on similar methods of immobilizing stable and regenerable molecules onto low energy, non-fouling substrates. In this regard, an expanded Teflon® tube which is initially metallized on the exterior by any number of well known methods can be modified on the interior using hydrogen/vapor (water or methanol) RFGD plasma treatment to form an oxyfluorinated surface on the tube interior. The tube is treated to a hydrolysis reaction supra., in order to directly immobilize a specific lectin molecule which derives from a special class of natural binding proteins. This produces a monolayer to a sub-monolayer of lectin molecules covalently immobilized through carboxylic acid moieties inherently contained within their parent structure.

Lectins belong to a special class of natural binding proteins that recognize certain carbohydrate units. Thus, some proteins can couple with polysaccharide structures, smaller sugar molecules, e.g., glucose, fructose, etc., or larger proteins which possess innate carbohydrate substructures (glycoproteins). For sensing or separation purposes, lectins offer an advantage when compared to antibodies and other natural binders in that their affinity constraints are somewhat lower than the other classes of receptor proteins. In most cases this implies faster dissociative kinetics permitting sensors based on these proteins to be truly reversible, which is ideal for chromatographic separations.

Using the expanded PTFE tube as modified it is then possible to facilitate chromatographic separations of molecules containing carbohydrate units. Binding of these carbohydrate units to a particular lectin protein is pH dependent so various separations using liquid chromatographic techniques can be performed by using aqueous mobile phases buffered to various pHs. Advantages of using the expanded PTFE tube or column instead of a conventional silica packed chromatographic column include the advantages previously described, i.e., non-fouling, stability and regenerability. In addition, due to the microporous surface morphology of the polymer it typically has surface areas ranging from at least one to three orders of magnitude greater than silica packed columns normally used in liquid chromatographic separations. This increase in surface area can be use to greatly decrease separation time, or in cases where the column is hooked up to a detector sensitive to carbohydrates chromatographic analysis time is greatly decreased. Alternatively, one can also use this surface area advantage to construct a micro separation column capable of in vivo applications, e.g. in vivo glucose sensor.

The protein-containing substrates of the invention can be employed in sensors and probes, for example, and particularly fibre optic types based on antibodies. One example would be immunoprobes having a surface immobilized antibody fragment labeled with an environmentally sensitive fluorophore, such as dansyl chloride, and used as a chemical recognition element. Coupling the protein to the substrate can be achieved through the carboxylic acid functionality contained in the biologically active molecules by reacting with the hydroxyl groups of the oxyfluorinated surface via hydrolysis coupling. The bioreactive molecule reacts with the hydroxyl groups of the oxyfluorinated surface in the presence of potassium carbonate in DMSO at 60° C.

Alternatively, coupling of biologically active or bioreactive molecules can be performed through their amine functionalities with subsequent covalent bonding to the hydroxyl functionality of the oxyfluorinated surface via a vinyl sulfone coupling reaction, described in greater detail below.

The following specific examples demonstrate the various aspects of this invention, however, it is to be understood that they are for illustrative purposes only, and do not support to be wholly definitive as to conditions and scope.

EXAMPLE I

Part A

To prepare oxyfluoropolymers, using radio frequency glow discharge (RFGD) a model PDC-23 g RF plasma chamber having maximum output of 100 watts from Harrick Scientific Corp., Ossining, N.Y., was modified by adding an in-line VG Model MD 95 ultra high vacuum (UHV) leak valve before the inlet side of the glow discharge unit. The UHV leak valve provided precise control of the system pressure while also allowing smooth flow of vaporized liquids into the plasma reaction chamber. In addition, a diffusion pump in conjunction with a roughing pump was installed at the outlet of the plasma reaction chamber. Optionally, a liquid nitrogen trap can be installed between the RFGD unit and the diffusion pump from potentially damaging vapors. Hydrogen from a flow meter, and liquids, e.g., water, methanol, formaldehyde, etc., are bled by the UH vacuum release valve to the inductively coupled plasma reaction chamber.

Through use of the diffusion pump, a base pressure of about 5 mTorr was obtainable and employed before all glow discharge treatments to effectuate a clean experimental system. By ultra-sonically extracting the samples in hexane, all trace contaminants caused by backflow of pump oil was minimized. In addition, by ultra-sonically cleaning the samples, low molecular weight and evanescent surface constituents were effectively removed. This permitted more accurate analysis of permanent surface functionalities introduced into the fluoropolymer through RFGD surface modification.

Part B

A sheet of porous PTFE (Goretex) measuring 10 cm×5 cm×1mm was analyzed using high resolution (17.9 eV) electron spectroscopy for chemical analysis (ESCA) to establish the true atomic percentages of carbon and fluorine present in the sample prior to glow discharge treatment. Measured peak areas of the detected atoms (carbon and fluorine) using atomic sensitivity factors gave corrected atomic percentages of 70% fluorine and 30% percent carbon for the sample corresponding to a $C_{1.0}F_{2.3}$ stoichiometry and a molecular structure $CF_3$—$(CF_2)$—$_n$. . . . .—$CF_3$. Corrected binding energies of the carbon and fluorine is peaks indicated a totally saturated carbon backbone with no detectable oxygen.

The pure perfluorinated sheet was then placed on the sample stage in the plasma reaction chamber and exposed for 20 minutes at 100 watts to a gas/vapor RFGD plasma mixture consisting of ca. 98% volume hydrogen and ca. 2% by volume water at 150 mTorr pressure. The sample was then subjected to ESCA analysis. The low and high resolution surveys showed C 1s, F 1s and O 1s results indicating the molecular structure. C is indicated the incorporation of large amounts of aliphatic C—H and —$CH_2$—$CH_2$— functionality with lesser amounts of carbon-oxygen functionality. Elemental analysis showed C 33.3%; F 22.2%; H 40.0%; O 4.5%. ATR-Infrared spectroscopic results indicated the formation of both C—O and —OH functionality.

EXAMPLE II

A second sample of the same pure porous PTFE sheet of Example I, Part B and of the same dimensions was exposed to a gas/vapor RFGD plasma mixture also consisting of 98% by volume hydrogen and 2% by volume water at 100 watts and a pressure of 200 mTorr like that of Example I, Part B. However, the exposure time was decreased from 20 to 10 minutes. The ESCA low resolution survey and high resolution C 1s, and O 1s spectra showed the addition of oxygen and hydrogen to the molecular structure of the PTFE surface. An ATR-IR spectrum of this material also indicated incorporation of amounts of C—O and —OH functionality onto the surface portion of the sheet. Elemental analysis showed C 33.3%; F 37.3%; H 25.5%; O 3.9%.

EXAMPLE III

A sheet of shear porous PTFE (Goretex) like that used in Examples I and II was exposed to a gas/vapor RFGD plasma mixture using the laboratory set-up described above in Part A of Example I. The plasma consisted of 80% by volume hydrogen and 20% by volume methanol. Exposure time was 30 minutes at a pressure of 150 mTorr. The ESCA low resolution and high temperature C 1s, F 1s, O 1s spectra showed the introduction of oxygen at the molecular level on the PTFE surface. The C 1s ESCA spectrum indicated both aliphatic carbon and C—O functionality with a corresponding decrease in fluorinated carbon groups. The F 1s spectrum showed a large increase in peak width, indicative of two types of fluorine functional group environments residing at the PTFE surface region. The amount of oxygen functionality present in the modified oxyfluoropolymer surface was more than double that of the samples prepared in Examples I and II, as shown by the following elemental analysis: C 33.3%; F 22.0%; H 33.3%; O 11.1%. ATR-IR showed a corresponding increase in C—O and —OH functionality.

EXAMPLE IV

A sheet of polyvinylidene fluoride (PVDF) measuring 10 cm×5 cm ×1 mm was analyzed using high resolution ESCA to establish the composition of the sample. Two peaks of almost equal area were observed which were indicative of a molecular structure containing equal amounts of $CH_2$ and $CF_2$ groups. The unmodified polymer can be described as $C_{1.0}F_{1.0}H_{1.0}$ with a molecular structure of $(CH_2$—$CF_2)_n$—. The unmodified PVDF sheet had an elemental analysis of C 33%; F 33%; H 33%.

The sample sheet of PVDF was exposed to a gas/vapor RFGD plasma mixture for 10 minutes at a pressure of 200 mTorr at 100 watts in the laboratory set-up of Example I, Part A. The gas/vapor mixture consisted of 2% by volume water and 98% by volume hydrogen. The treated sample was then analyzed using ESCA low resolution survey and high resolution C 1s, F 1s and O 1s which demonstrated an extreme drop in the fluorine signal with a corresponding increase in hydrogen and oxygen to the top surface to a depth of about 100 Å. The C 1s spectrum indicated a hydrocarbon surface with some C—O functionality and little or no C—F functionality in the top most 100 Å of the PVDF surface. ESCA analysis indicated only 2 atomic percent fluorine in the upper most 100 Å of the modified material whereas the original unmodified sheet contained 33 atomic percent fluorine. Elemental analysis of the treated PVDF was C 33.3%; F 2.1%; H 60.4%; O 4.2%.

EXAMPLE V

A sample of the same pure PTFE used in Example I, Part B, was exposed to a gas/vapor RFGD plasma mixture consisting of about 60% by volume hydrogen and 40% formaldehyde for 5 minutes at a pressure of 200 mTorr at 100 watts in the laboratory set-up of Example I, Part A. Elemental analysis by ESCA of the treated PTFE was found to be C 33.3%; F 16.7%; H 46.4%; O 3.6%. ATR-IR again indication formation of C—O and —OH functionality.

EXAMPLE VI

Modified fluoropolymer materials (Table II below) were analyzed using a wettability profile which measures the contact angles of various liquids each having a different surface tension. This series of liquids with different surface tensions allows for the measurement of changes in wettability as related to an empirical measure of surface energy. Further, the change in hydrophilicity/hydrophobicity can also be measured through use of the higher surface tension polar liquids (i.e., water and glycerol). The critical surface tension ($\gamma_c$) is the value given indicating the surface tension of the liquid which totally spreads on the surface in question. Liquids with surface tensions equal to or below this value will also be observed to spread, and thus, increase in $\gamma_c$ relate an increase in surface energy allowing for greater wettability of liquids with higher surface tensions.

The contact angles of the various liquids listed in Table II were measured on each respective material employing a model 100 Rame' Hart Gonimeter for measuring the angle and a freshly flamed Pt wire for placing the purified liquid drops on the material surfaces.

Table II shows that a decrease in contact angles as measured on the 20 minutes $H_2/H_2O$ RFGD modified Goretex was small for the liquids having surface tensions >39.3 dynes/cm indicating a retention of the original materials non-wetting characteristics for these liquids. The measured angles for these liquids also indicate the retention of surface residing fluorine functionality and especially a large degree of hydrophobicity as indicated from the angles measured for water and glycerol. Below 39.3 dynes/cm, the contact angles of the utilized liquids showed a larger degree of wettability indicating an increase in surface energy which is ascribed to the presence of small amounts of surface residing oxygen functionality earlier detected by ESCA and IR results. A 0° measurement (i.e., $\gamma_c$) was observed at 27.6 dynes/cm for the $H_2/H_2O$ RFGD modified Goretex as compared to 23.8 dyne/cm as measured on the unmodified Goretex membrane. This indicates an increase in surface energy again, attributed to the creation of surface residing oxygen functionality in close proximity to the fluorine functionality.

Similar observations were made on the PVDF modified material except that the surface energy showed a greater degree of enhancement (i.e., $\gamma_c$ increased from 27.6 dyne/cm as measured on unmodified PVDF to 39.3 dyne/cm for the $H_2/H_2O$ RFGD modified PVDF). Again, the degree of hydrophobicity showed only minor decreases as indicated by >90° (110°) measured contact angle of water on the modified PVDF surface.

These two examples illustrate only the values for $\gamma_c$ of modified materials and measurements achieving a range of $\gamma_c$ values (from 25–40 dyne/cm have been observed for the Goretex modified materials and 30–40 dyne/cm for the modified PVDF materials) which are dependent on RFGD conditions especially hydrogen/vapor concentration and the liquid employed as the vapor.

EXAMPLE VII

A bioprobe may be fabricated for detecting various molecules or important species in a biological system, e.g. kidney. A very low surface energy fluoropolymer, such as porous PTFE, e.g., Goretex membrane, would be suitable starting material where total inertness is desired. However, a bioprobe would be especially desirable in this instance if

TABLE II

| | Measured Contact Angles (degrees) | | | | |
|---|---|---|---|---|---|
| | LIQUID/VAPOR SURFACE TENSIONS (dyne/cm) | UNMODIFIED PTFE GORTEX | MODIFIED PTFE 20 min $H_2(H_2O)$ EXAMPLE II | UNMODIFIED PVDF | MODIFIED PVDF 10 min $H_2(H_2O)$ EXAMPLE IV |
| Water | 72.4 | –140° | 110° | 120° | 110° |
| Glycerol | 64.8 | 130° | 115° | 125° | 115° |
| Formamide | 58.9 | 130° | 112° | 115° | 95° |
| Thiodiglycol | 53.5 | 125° | 120° | 107° | 80° |
| Methylene Iodide | 49.0 | 120° | 115° | 102° | 25° |
| 1-Bromo-Napthalene | 45.0 | 100° | 110° | 40° | 10° |
| 1-Methyl-Napthalene | 39.3 | 100° | 90° | 10° | (spread) 0° |
| Dicyclohexyl | 32.7 | 93° | 60° | 10 | 0° |
| n-Hexadecane | 27.6 | 20° | (spread) 0° | 5° | 0° |
| n-Tridecane | 26.0 | 10° | 0° | (spread) 0° | 0° |
| n-Decane | 23.8 | (spread) 0° | 0° | 0° | 0° | ion permeability was enhanced without changing the membrane's pore structure or hydrophobic character, and at the same time the majority of the probe would remain essentially inert and nonreactive so as to prevent contamination or bio-rejection when placed in-vitro. This may be accomplished by the removal of fluorine atoms and the incorporation of —OH functionality into the PTFE. Other moieties may then be introduced by reacting with these sites. Silanes, for example, may be quickly reacted with such oxygen functionalities by formation of the Si—O bond. Accordingly, through known masking techniques several modified sites may be created by exposing the polymer to gas/vapor RFGD plasma mixtures as disclosed above. Furthermore, using known masking techniques each of the modified sites may be reacted with a silane having different chemical and/or physical characteristics. Each of these silanized sites would also be isolated from one another due to the unmodified inert PTFE material surrounding each site. The modified material would then be useful in fabricating the bioprobe.

EXAMPLE VIII

A 10×20 cm² piece of expanded (e)PTFE (Goretex membrane material) and PTFE (smooth solid sheet) were exposed for 30 minutes to a $H_2$/methanol RFGD plasma, and subsequently dipped in and out; dipped for 1 minute; dipped for 10 minutes; dipped for 30 minutes; refluxed for 15 minutes and then refluxed for 4 hours in a one percent aminopropyltriethoxysilane (APTES) in a 99% hexane solution. Electron spectroscopy for chemical analysis (ESCA) results are listed in Table III below:

TABLE III

ESCA ATOMIC RATIOS
(APTES refunctionalized Oxy. fluoro materials)

| Sample | C/F | C/O | Si/F | Si/N |
|---|---|---|---|---|
| Unmodified ePTFE | 0.43 | — | — | — |
| 30 min. $H_2$/MeOH RFGD oxy. fluoro ePTFE | 0.93 | 15.0 | — | — |
| Quick dip of oxy. fluoro ePTFE in APTES | 1.22 | 4.1 | 0.17 | 0.95 |
| 1 minute dip | 1.53 | 4.0 | 0.21 | 0.98 |
| 10 min. dip | 1.51 | 3.1 | 0.27 | 0.99 |
| 30 min. dip | 2.4 | 2.6 | 0.54 | 1.05 |
| 15 min. reflux of oxy. fluoro ePTFE in APTES | 9.4 | 2.1 | 2.93 | 0.97 |
| 4 hour reflux | — | 2.1 | — | 1.03 |
| Unmodified PTFE | 0.48 | — | — | — |
| 30 min. $H_2$/MeOH RFGD oxy. fluoro PTFE | 1.5 | 8.7 | — | — |
| Quick dip in APTES | 1.8 | 3.3 | 0.23 | 0.97 |
| 10 minute dip | 2.86 | 3.1 | 0.44 | 0.93 |
| 30 minute dip | 2.24 | 3.1 | 0.40 | 0.99 |

The data in Table III indicate a polymer surface comprising both silane and fluorine functionality with increasing silane (observed through increases in the Si/F ratios) as a function of dip time in the APTES/hexane solutions. Exposure to the APTES/hexane solutions under refluxing conditions allowed for the formation of a thick overcoating of APTES such that no signal from the underlying e-PTFE was observed, i.e., total coverage of the e-PTFE is facilitated. The Si/N atomic ratios as provided in Table III show the retention of the origanosilicon molecular unit in that the corrected ratio is calculated to be within error limits 1.00, i.e., the expected atomic ratio for APTES. On all samples vigorous washing in a variety of polar and non-polar solvents (including hexane, methanol, chloroform and THF) were performed immediately following refunctionalization and up to six months later with no detection of change in the refunctionalized surfaces, illustrating the permanency and stability of the refunctionalized oxyfluorinated materials. Further, in all cases a piece of the unmodified original ePTFE material was treated identically as a control and no detection of silanization or addition of oxygen was observed, i.e., ESCA results gave atomic ratios identical to those normally found for unmodified PTFE or ePTFE materials with no detection of silicon or oxygen.

All of the modified/refunctionalized materials (except those refluxed for the 4 hour period) showed an extremely high hydrophobic character, i.e., contact angles of polar liquids, including water, formamide and glycerol were all >110° (see Table IV below). The materials refluxed for 15 minutes and for 4 hours (which from ESCA results showed total coverage) were observed to have increased wettability characteristics tending towards but not completely approaching those associated with pure APTES films.

TABLE IV

WETTABILITY DATA

| Liquid | Surface Tension dynes/cm | Contact Angle θ as measured on each sample | | | | |
|---|---|---|---|---|---|---|
| | | 1 | 2 | 3 | 4 | 5 |
| Water | 72.4 | 148 | 117 | 66 | 110 | 90 |
| Glycerol | 64.8 | 151 | 100 | 63 | 126 | 85 |
| Formamide | 58.9 | 123 | 112 | 40 | 115 | 80 |
| Thiodiglycol | 53.5 | 133 | 112 | 35 | 35 | 85 |
| Methylene Iodide | 49.0 | 128 | 81 | 38 | 33 | 40 |
| S-Tetrabromoethane | 49.8 | 125 | 76 | — | — | — |
| 1-Bromo-naphthalene | 45.0 | 114 | 0 | 25 | 40 | 10 |
| o-Dibromo-benzene | 43.3 | 118 | 0 | — | — | — |
| Propylene Carbonate | 41.8 | 119 | 0 | — | — | — |
| 1-Methyl naphthalene | 39.3 | 97 | 0 | 15 | 45 | 0 |
| Dimethyl-formamide | 37.5 | 113 | 0 | — | 0 | 0 |
| Dicyclohexyl | 32.7 | 66 | 0 | 6 | 0 | 0 |
| n-Hexadecane | 27.6 | 35 | 0 | 0 | 0 | 0 |
| n-Tridecane | 26.0 | 0 | 0 | 0 | 0 | 0 |

1. unmodified ePTFE
2. 30 minute $H_2$/MeOH RFGD oxy. fluoro PTFE membrane
3. APTES Film
4. Oxy.fluoro membrane dipped in 1% APTES/99% Hexane for 15 minutes
5. Oxy.fluoro membrane refluxed for 15 minutes in APTES solution

EXAMPLE IX

A similar study to that described in Example VIII was conducted, but instead of employing the silane APTES, a 3-mercaptopropyltrimethoxysilane (MPTMS) was utilized. Without using a solid smooth PTFE, an original sample of expanded ePTFE material (Goretex) was modified by forming an oxyfluorinated material according to the foregoing examples using a 20 minute $H_2$/water RFGD treatment. The results identified by ESCA are provided in Table V below. Similar to the results listed in Example VIII, the data show increased amounts of MPTMS with an increase in exposure time, however, an ever present amount of fluorine surface functionality resulted in a very hydrophobic refunctionalized surface.

TABLE V

ESCA ATOMIC RATIOS
(MPTMS refunctionalized oxy.fluoro materials)

| Sample | C/F | C/O | Si/F | Si/S |
|---|---|---|---|---|
| Unmodified ePTFE | 0.43 | — | — | — |
| 20 min. $H_2/H_2O$ RFGD oxy.fluoro ePTFE | 0.65 | 16.0 | — | — |
| Quick dip of oxy. fluoro ePTFE in APTES | 0.77 | 12.3 | 0.06 | 1.03 |
| 1 minute dip | 0.73 | 11.0 | 0.08 | 1.00 |
| 5 minute dip | 0.80 | 11.6 | 0.07 | 1.05 |

EXAMPLE X

A similar study to that of Example VIII was performed using glycidoxypropyltrimethoxysilane (GPTMS). The polymer employed was PTFE (Teflon® tape) modified by a 30 minute treatment to a $H_2$/methanol vapor RFGD. The films were dipped for one minute in a 1% GPTMS/99% hexane solution and a 1% GPTMS/1% acetic acid/98% hexane solution. This was done in order to determine the effect of pH change on reaction rate. It will be noted from the ESCA analysis that Si/F atomic ratios (Table VI below) that the extent of the reaction is greatly enhanced by increasing the acidity of the silane solution. This feature then predicts the use of the modified oxyfluorinated materials as pH sensitive membrane materials, i.e. pH sensors.

TABLE VI

ESCA ATOMIC RATIOS
(GPTMS refunctionalized Oxy.fluoro materials)

| Sample | C/F | C/O | Si/F |
|---|---|---|---|
| Unmodified ePTFE | 0.43 | — | — |
| 30 min. $H_2$/MeOH RFGD oxy.fluoro ePTFE | 0.90 | 10.01 | — |
| Quick dip of oxy-fluoro ePTFE in a 1% GPTMS: 99% Hexane solution | 1.11 | 4.2 | 0.07 |
| Quick dip of oxy. fluoro ePTFE in a 1% GPTMS: 1% Acetic acid: 98% Hexane solution | 11.1 | 1.71 | 1.68 |

EXAMPLE XI

Expanded PTFE and solid smooth films of PTFE were prepared as in Example VIII, i.e., the films coated with APTES from a quick dip; 15 minute dip and a 30 minute dip, were exposed for 24 hours to the fluorophore, fluorescein isothiocyanate (FITC), which at a pH of 10 reacts preferentially with amine functionality, i.e., the FITC was used to label the free amines of the APTES location on the APTES-oxyfluorinated surface. The FITC fluorescent molecule and laser fluorescence data (See Table VII below) show the increase in bonded FITC as a function of increase in APTES.

TABLE VII

Surface fluorescence intensity (background subtracted)
and
Surface Concentration of FITC
Reacted to APTES Amine Functionality
On a Oxy.Fluoro/APTES ePTFE Membrance

| Sample | Fluorescence intensity | Surface Concentration |
|---|---|---|
| Unmodified ePTFE | 0.00 | 0.00 |
| FITC reacted to oxy. fluoro ePTFE quick dipped in APTES | 1.22 | 2.89 nmol/cm$^2$ |
| FITC reacted to oxy. fluoro ePTFE dipped in APTES for 1 minute | 1.34 | 3.17 nmol/cm$^2$ |
| FITC reacted to oxy. fluoro ePTFE dipped in APTES for 5 minutes | 1.45 | 3.44 nmol/cm$^2$ |
| FITC reacted to oxy. fluoro ePTFE dipped in APTES for 15 minutes | 1.82 | 4.31 nmol/cm$^2$ |

EXAMPLE XII

At a pH of 10, FITC was observed by both ESCA (observed through the N/F and S/F ratios listed in Table VIII below) and laser fluorescence spectroscopy to react directly, i.e., without the APTES amine present to oxyfluorinated material modified by exposing expanded (e) PTFE (Goretex) and Teflon (PTFE) tape for 30 minutes to RFGD and a plasma consisting of $H_2$/methanol and 20 minutes to $H_2/H_2O$. This was an unusual result considering FITC's normal reactivity limitation to basic amines. This provides evidence for the existence of a strong anionic oxygen (O$^-$) on the oxyfluorinated surface, and further suggests the reactivity to all atoms and/or molecules which show reactivity to strong O$^-$ sites.

TABLE VIII

ESCA ATOMIC RATIOS
(FITC reacted to oxy.fluoro ePTFE)

| Sample | C/F | C/O | N/F | S/F |
|---|---|---|---|---|
| Unmodified ePTFE | 0.43 | — | — | — |
| 30 min. $H_2$/MeOH RFGD oxy.fluoro ePTFE | 0.90 | 10.0 | — | — |
| Oxy.fluoro ePTFE placed in FITC solution pH = 10 for 24 hours | 1.40 | 3.60 | 0.05 | 0.05 |

EXAMPLE XIII

Further testing for the presence of a strong oxygen group on the oxyfluorinated surfaces was performed by using an (e)PTFE starting material and modifying its surface with a 30 minute treatment to a radio frequency glow discharge mixture of hydrogen/ methanol, so as to create an oxyfluorinated surface. This material was ultrasonicated in concentrated sodium hydroxide for 30 seconds using one piece as modified and another modified piece first rinsed in methanol before transference to the sodium hydroxide solution. Due to extreme hydrophobicity previously indicated for oxyfluorinated surfaces, the sample which was not first wet with non-polar methanol did not sink into the sodium hydroxide solution. This material was forcibly clamped into the sodium hydroxide solution during the 30 second ultrasonication. The material first wet with methanol had the ability to enter the sodium hydroxide solution, and thus, did not need clamping. ESCA results listed in Table IX below indicate the ionic exchange which occurred between the oxyfluorinated surface and the sodium hydroxide solution. That is, the formation of a Na-O-ePTFE which from ESCA results occurs to a much greater extent on the material first wet with methanol. Only superficial Na-O-bonding is noted on the material which required clamping into the sodium hydroxide solution. These results indicate the oxyfluorinated polymer and subsequently refunctionalized oxyfluorinated material as ion exchange solid support membranes, particularly in the case of expanded PTFE (Goretex). Furthermore, due to the extreme hydrophobic nature of these materials as observed from the oxyfluorinated material not first wet in methanol, the membranes would be useful as battery separator/membranes in cases where ion exchange without water or aqueous flow through a membrane is required. For example, high energy density batteries using lithium based electrodes are limited largely due to the need for a membrane which requires ion exchange from the lithium to an aqueous electrolyte without aqueous electrolyte coming in contact with the lithium metal.

TABLE IX

ESCA ATOMIC RATIOS
(NaOH reacted to oxy.fluoro ePTFE)

| Sample | C/F | C/O | Na/F |
| --- | --- | --- | --- |
| Unmodified ePTFE | 0.43 | — | — |
| 30 Min. H$_2$/MeOH RFGD oxy.fluoro ePTFE | 0.88 | 14.2 | — |
| Oxy.fluoro ePTFE ultrasonicated in concentrated NaOH for 30 seconds | 0.84 | 4.1 | 0.08 |
| Oxy.fluoro ePTFE ultrasonicated in concentrated NaOH for 30 seconds after pre-wetting in methanol | 2.7 | 2.5 | 0.57 |

EXAMPLE XIV

Polyethylene is frequently employed in the fabrication of containers for water and other beverages. In some instances, long term storage is complicated by algae formations, proteinaceous and other mold based films causing discolorment and imparting of unpleasant taste to stored liquids. Modifying the interior polyethylene surface of the container by applying a fluorocarbon film by gas phase fluorination followed by oxyfluorination one can then refunctionalize the interior with a methylated ligand-containing silane coupling agent which resists and inhibits the formation of molds, algae and other proteinaceous films.

Part A—Fluorination

A gas phase fluorination reactor system or "GPFRS" is commercially available, and is similar to that described by R. J. Lagow and J. L. Margrave, *Progr. Inorganic Chem.* Ed., S. J. Lippard, 26, 161 (1979). The GPFRS permits the surface fluorination of a variety of commercially available polymeric films. A 10 percent or less fluorine gas/90 percent or more nitrogen gas mixture is controllably bled through a series of flowmeters to control the amount of fluorine gas in a background of nitrogen. Once the mixture has been controlled it is bled into the reaction chamber containing the polyethylene container.

Part B—Oxyfluorination

Once the container has been surface fluorinated it can then be oxyfluorinated by introducing into a radio frequency glow discharge (RFGD) plasma reactor and exposed to a H$_2$/H$_2$O or H$_2$/methanol gas plasma according to the methodology of Example I. The interior surface of the container will exhibit the properties of an oxyfluorinated material, as previously described.

Part C—Refunctionalization

The oxyfluorinated surface of the container can be refunctionalized with different chemistries by reacting with an organosilane coupling agent containing a particular organoligand group. This can be performed by placing the oxyfluorinated container so it is contact with aqueous or organic solvents which contain the particular organosilane coupling agent. Covalent bonding of the organosilane coupling agent is achieved by either spontaneous hydrolysis and coupling through the hydroxyl groups on the oxyfluorinated surface, or through refluxing for a period of time to enhance the hydrolysis reaction. The thickness of the organosilane film on the substrate/polyethylene container can be controlled by exposure times and refluxing conditions.

EXAMPLE XV

This example relates to the preparation of polymethylmethacrylate optical windows for an antibody based fiber optic sensor. Antibody based fiber optic fluorescence sensors employ a quartz window at the distal end of the fiber optic. The quartz window has a fluorescently labeled antibody such that the fluorescence signal as measured through the fiber optic conduit changes quantitatively as the corresponding antigen to the antibody is recognized and bound to the immobilized antibody on the quartz substrate.

The inherent problems with this probe are that, due to the high surface energy of the quartz material, immobilized antibodies rapidly denature making the probe unusable after a few days to a week, as well as severely limiting the reusability via regeneration of the probe. By employing a surface fluorinated polymethylmethacrylate window a low energy substrate with the appropriate optical clarity can be constructed which will inhibit antibody denaturation, thus increasing the longevity and reusability of such an antibody based fiber optic fluorescence sensor.

Following the steps of Parts A and B of Example XIV, a polymethylmethacrylate optical window is surface fluorinated and oxyfluorinated. The surface oxyfluorinated substrate is then refunctionalized with biologically active or bioreactive molecules. The expressions "biologically active" and "bioreactive molecule" are intended to encompass ionophores, ion-exchangers, enzymes, antibodies, antigens, lectins, neurochemical receptors, oligonucleotides, polynucleotides, polypeptides, molecules of DNA, molecules of RNA, proteins, glycoproteins, metalloproteins, co-factors, immunoglobulins, and other macromolecules of physiological significance, including mixtures, fragments or sub-units thereof.

Coupling Biologically Active or Bioactive Molecules:

Direct coupling of the amine functionality in the biologically active or bioreactive molecules with subsequent covalent attachment to the hydroxyl functionality of the oxyfluorinated polymethylmethacrylate surface is performed by a vinyl sulfone coupling reaction. With vinyl sulfone coupling the polymeric material with the modified oxyfluorinated surface is first activated by immersing into a 1M sodium carbonate solution at a pH 10 to which 20% by volume vinyl sulfonic acid (sodium salt) is added. The materials are then incubated for at least 70 minutes, but optimally for 2–3 days at room temperature, and then washed in 0.1M Tris pH 7. Coupling of the bioreactive molecule through a contained amine functionality is then accomplished by immersing the activated materials into sodium carbonate pH 10 which contains the bioreactive molecule. The reaction then proceeds for at least 24 hours at 4° C. The reaction is then quenched by removal from the solution and placement into three changes of 1% glycine in 0.1M Tris pH 7, and two changes of 0.1M Tris pH 7.

EXAMPLE XVI

Non-fluorinated substrates comprising polymers, metals, metal alloys and ceramics are coated with plasma polymerized films generated from fluorine-containing gases, such as hexafluoropropane, hexafluoroethane or hexafluoropropene. The nonfluorinated substrate material is placed within either a capacitatively or inductively coupled radio frequency glow discharge generator. After achieving a vacuum of ca. 10 mTorr one of the above fluorinated gases is introduced at pressures ranging from 100 mTorr to 500 mTorr for systems which operate between 20 and 100 watts. While it may be possible to operate outside these ranges pressures will depend on capabilities of the radio frequency generator chamber size. Thickness of deposited films are a function of exposure times, but can be monitored by including a vibrating quartz crystal deposition monitor (Inficom XTM) inside the reaction chamber. The fluorocarbon coated non-fluorinated substrate may then be oxyfluorinated and refunctionalized according to the methods described, for example, in Parts B and C of Example XIV above.

EXAMPLE XVII

An expanded ePTFE separation column for human serum albumin is prepared with an ePTFE 10 cm tube with an i.d. of 50 µm first metallized on the outside by immersing for 5 minutes in Metex® 9027 brand electroless copper plating bath prepared in accordance with the manufacturer's direction for using. This provides an ePTFE tube having a copper coating on the outside with an unmodified ePTFE inner core. The tube is then placed into an RFGD hydrogen/methanol plasma for 2 minutes to oxyfluorinate the surface of the interior walls of the tube. The tube is then placed for 24 hours in a solution of DMSO containing 1 mg of potassium carbonate and 10mg of anti-human serum albumin at 60° C. Upon removal the tube is washed in a clean solution of DMSO, methanol, and distilled deionized water. The tube is then ready for use as a liquid chromatograph column for separating and quantitating serum human albumin from a variety of matrices, e.g., blood and blood plasma.

EXAMPLE XVIII

An electrochemical immuno-sensitive sensor is prepared by placing a platinum electrode in a capacitively coupled (13.56 MHz r.f. generator) plasma fluoropolymer deposition chamber which has been evacuated to 0.02 Torr. Using a mass flow-controlled gas blender, such as a Linde FM4590, the monomer gas perfluoropropane ($C_3F_8$) is introduced into the chamber under dynamic flow conditions such that a constant pressure of 0.3 Torr is achieved. Upon reaching constant pressure conditions the r.f. generator is activated to produce a plasma which in turn deposits a fluoropolymer film with a thickness of 0.1 µm on the platinum electrode. The electrode is removed and washed in methanol. The electrode is placed in an inductively coupled r.f. plasma treatment chamber and modified with a hydrogen/methanol plasma to produce an oxyfluorinated surface. The modified platinum electrode is then introduced into a 60° C. solution of DMSO containing 1 mg of potassium carbonate and 10 mg of Concanavalin A (a lectin for specifically binding the polysaccharide yeast mannan). The tube is then washed in a clean solution of DMSO, methanol, and finally distilled deionized water. The platinum electrode can be used to measure emf changes as a function of yeast mannan binding to the Concanavalin immobilized on the electrode surface.

EXAMPLE XIX

An immunochemically sensitive field effect transistor (IMFET) sensor for Wassermann antigen (syphilis test) is fabricated by placing an IMFET into a reaction chamber according to that described in Example II where the only difference is that a mask is applied so that deposition of the plasma fluoropolymer is limited to the metal oxide (tin or copper oxide) gate of the field effect transistor. The deposited plasma fluoropolymer is then modified according to the method of Example II to form an oxyfluorinated surface on top of the metal oxide gate. The modified IMFET is then introduced for 24 hours into a 60° C. solution of DMSO containing 1 mg potassium carbonate and 10 mg of Wassermann's antigen which is selective with respect to binding antibodies for detection of syphilis. Upon removal the IMFET is washed in a clean solution of DMSO, methanol, and finally distilled deionized water. The IMFET can then be employed to measure concentrations of antibodies related to syphilis from various biological fluids, including blood and blood plasma.

The invention has been described in conjunction with specific examples thereof. They are illustrative only. Accordingly, many alternatives, modifications and variations will be apparent to those skilled in the art in light of the foregoing description, and it is therefore intended to embrace all such alternatives, modifications and variations as to fall within the spirit and broad scope of the appended claims.

We claim:

1. An oxyfluorinated substrate comprising a non-fluorinated material selected from the group consisting of polymeric, ceramic and metallic materials, the surface of said polymeric material modified with (a) molecularly bonded fluorine atoms, or (b) a fluorocarbon film, the surface of said ceramic and metallic materials modified with a fluorocarbon film, the modified surfaces having up to 98 percent of their fluorine atoms to depths from about 10 to about 100 Å permanently substituted with hydrogen and oxygen or oxygen-containing groups to form substrates with oxyfluorinated surfaces of which from about 3 to about 30 percent of the substituted fluorine is replaced with oxygen or oxygen-containing groups and from about 70 to about 97 percent of the fluorine is replaced with hydrogen atoms, the morphological and hydrophobic properties of the oxyfluorinated surfaces remaining substantially unchanged from that of the unmodified surfaces having said fluorine atoms and fluorocarbon films while wettability with respect to low surface tension liquids and surface free energy ($\gamma_s$) as determined through critical surface tension ($\gamma_c$) are increased.

2. The oxyfluorinated substrate of claim 1 wherein the non-fluorinated material is a polymer selected from the group consisting of thermoplastic and thermosetting polymers in the form of fibers, films or sheets.

3. The oxyfluorinated substrate of claim 2 wherein the non-fluorinated material is a thermoplastic selected from the group consisting of a polyolefin, polyester, acrylic resin, polycarbonate resin, polyurethane, polystyrene and PVC.

4. The oxyfluorinated substrate of claim 1 wherein said fluorocarbon film is a fluorocarbon polymer or fluorohydrocarbon polymer.

5. The oxyfluorinated substrate of claim 4 wherein said fluorocarbon film is plasma deposited and selected from the group consisting of hexafluoroethane, perfluoropropane and hexafluoropropene.

6. The oxyfluorinated substrate of claim 1 wherein the non-fluorinated material is a ceramic material selected from the group consisting of conductive, semiconductive and dielectric materials.

7. The oxyfluorinated substrate of claim 1 wherein the non-fluorinated material is a ceramic material based on oxides, carbides, nitrides and borides.

8. The oxyfluorinated substrate of claim 1 wherein the non-fluorinated material is a metal selected from the group consisting of gold, nickel, copper, aluminum, steel alloys, ferrous and nonferrous alloys.

9. A refunctionalized oxyfluorinated substrate, which comprises a non-fluorinated material selected from the group consisting of polymeric, ceramic and metallic materials, the surface of said polymeric material modified with (a) molecularly bonded fluorine atoms, or (b) a fluorinated film, the surface of said ceramic and metallic materials modified with a fluorocarbon film, the modified surfaces having up to 98 percent of their fluorine atoms to depths from about 10 to about 100 Å permanently substituted with hydrogen and oxygen or oxygen-containing groups to form substrates with oxyfluorinated surfaces of which from about 3 to about 30 percent of the substituted fluorine is replaced with oxygen or oxygen-containing groups and from about 70 to about 97 percent of the fluorine is replaced with hydrogen atoms, said oxyfluorinated surfaces being refunctionalized where from about 3 to about 100 percent of said oxygen or oxygen-containing groups have molecularly bonded thereto a member selected from the group consisting of an organosilane, an isothiocyanate-containing fluorescent compound and a protein.

10. The refunctionalized oxyfluorinated substrate of claim 9 wherein the protein is a member selected from the group consisting of an enzyme, antibody and a peptide.

11. The refunctionalized oxyfluorinated substrate of claim 9 wherein the non-fluorinated material is a ceramic selected from the group consisting of conductive, semiconductive and dielectric materials.

12. The refunctionalized oxyfluorinated substrate of claim 9 wherein the non-fluorinated material is a ceramic based on oxides, carbides, nitrides and borides.

13. The refunctionalized oxyfluorinated substrate of claim 9 wherein the non-fluorinated material is a metallic substance selected from the group consisting of gold, nickel, copper, aluminum, nickel alloys, steel alloys, ferrous and non-ferrous alloys.

14. The refunctionalized oxyfluorinated substrate of claim 9 wherein said fluorine atoms are covalently bonded to said substrate by gas-phase fluorination and the fluorocarbon coatings are plasma deposited.

15. A method of making a refunctionalized oxyfluorinated substrate which comprises the steps of:
   a) providing a non-fluorinated base material selected from the group consisting of a polymeric, ceramic and metallic materials;
   b) modifying the surface of:
      (i) said polymeric base material by a step selected from the group consisting of fluorination and coating with a fluorocarbon film;
      (ii) said ceramic and metallic material by the step of coating with a fluorocarbon film;
   c) oxyfluorinating the modified surface of (b) with a gas/vapor plasma mixture comprising hydrogen and at least one other member selected from the group consisting of water, methanol and formaldehyde while exposing said substrate to at least one radio frequency glow discharge under vacuum for a sufficient period to substitute at least a portion of the fluorine atoms on the substrate to a depth from about 10 to 100 Å with covalently bonded hydrogen and oxygen atoms or oxygen-containing groups, and
   d) refunctionalizing said oxyfluoroinated surface of (c) by reacting at least a portion of said oxygen atoms or oxygen-containing groups with a member selected from the group consisting of an organosilane, an isothiocyanate-containing fluorescent compound and a protein.

16. The method of claim 15 wherein the protein is a member selected from the group consisting of an enzyme, antibody and a peptide.

17. The method of claim 15 wherein fluorine atoms are covalently bonded to the substrate by gas-phase fluorination and the fluorocarbon coatings are plasma deposited.

18. The method of claim 15 including the step of masking portions of the modified surface of step (b) to form a pattern of covered and exposed surfaces, said exposed surfaces being oxy-fluorinated and refunctionalized according to steps c–d.

19. A method of making a patterned refunctionalized oxyfluorinated substrate, which comprises the steps of:
   a) providing a substrate comprising a fluorinated material;
   b) masking portions of the substrate of step (a) to form a predetermined pattern of covered and exposed surfaces;
   c) oxyfluorinating the masked surface of the substrate of step (b) by contacting with a gas/vapor plasma mixture comprising hydrogen and at least one other member selected from the group consisting of water, methanol and formaldehyde while exposing said substrate to at least one radio frequency glow discharge under vacuum for a sufficient period to substitute at least a portion of the fluorine atoms on the exposed surface to a depth from about 10 to 100 Å with covalently bonded hydrogen and oxygen atoms or oxygen-containing groups;
   d) refunctionalizing the substrate of step (c) by reacting at least a portion of said oxygen atoms or oxygen-containing groups on the exposed portions of the substrate with a member selected from the group consisting of an organosilane, an isothiocyanate-containing fluorescent compound and a protein.

* * * * *